(12) United States Patent
Hovdenakk

(10) Patent No.: US 10,966,509 B2
(45) Date of Patent: Apr. 6, 2021

(54) CARRYING BOX INTEGRATEABLE IN AN ARTICLE OF CLOTHING

(71) Applicant: Nexim AS, Sandnes (NO)

(72) Inventor: Björn Hovdenakk, Sandnes (NO)

(73) Assignee: Nexim AS, Sandnes (NO)

(*) Notice: Subject to any disclaimer, the term of this patent is extended or adjusted under 35 U.S.C. 154(b) by 161 days.

(21) Appl. No.: 16/078,398

(22) PCT Filed: Mar. 21, 2017

(86) PCT No.: PCT/NO2017/050073
§ 371 (c)(1),
(2) Date: Aug. 21, 2018

(87) PCT Pub. No.: WO2017/164748
PCT Pub. Date: Sep. 28, 2017

(65) Prior Publication Data
US 2019/0045909 A1    Feb. 14, 2019

(30) Foreign Application Priority Data

Mar. 21, 2016   (NO) .................................. 20160475
Mar. 13, 2017   (NO) .................................. 20170362

(51) Int. Cl.
*A45F 5/02*      (2006.01)
*A45C 11/00*     (2006.01)
(Continued)

(52) U.S. Cl.
CPC .............. *A45F 5/022* (2013.01); *A41D 27/20* (2013.01); *A44B 17/0005* (2013.01);
(Continued)

(58) Field of Classification Search
CPC ................ A41D 27/20; A41D 2400/48; A44B 17/0005; A44B 19/00; A44B 18/00;
(Continued)

(56) References Cited

U.S. PATENT DOCUMENTS 1,575,524 A      3/1926   Benjamin et al.
1,809,696 A  *   6/1931   Heilweil ................. A45C 11/22
                                                   206/37
(Continued)

FOREIGN PATENT DOCUMENTS

CA      2578127 A1 *  3/2006  ............. A61L 2/18
CA      2697834 A1 * 10/2010  ............. A61F 17/00
(Continued)

OTHER PUBLICATIONS

Norwegian Search Report, Norwegian Patent Application No. 20160475, dated Oct. 20, 2016.
(Continued)

*Primary Examiner* — Justin M Larson
*Assistant Examiner* — Lester L Vanterpool
(74) *Attorney, Agent, or Firm* — Andrus Intellectual Property Law, LLP

(57) ABSTRACT

A carrying box is releasably attachable to a portion of a piece of clothing. The carrying box has a top section connectable to a bottom section in a sealing manner. The bottom section has a curved bottom face with a curve radius substantially corresponding with the curve shape of a body part of a human being to be covered by the portion of piece of clothing. The carrying box further is arranged for releasable interconnection with said portion of piece of clothing by at least one attachment means, wherein at least one of a curved inward top face of the top section and the curved bottom face of the bottom section is arranged to carry a compress element.

15 Claims, 6 Drawing Sheets

(51) Int. Cl.
  *A41D 27/20* (2006.01)
  *A44B 17/00* (2006.01)
  *A61F 17/00* (2006.01)
  *A44B 18/00* (2006.01)
  *A44B 19/00* (2006.01)
  *A61F 13/00* (2006.01)

(52) U.S. Cl.
  CPC .............. *A44B 18/00* (2013.01); *A44B 19/00* (2013.01); *A45C 11/00* (2013.01); *A45F 5/02* (2013.01); *A61F 13/00072* (2013.01); *A61F 17/00* (2013.01); *A41D 2400/48* (2013.01); *A45C 2011/007* (2013.01); *A61F 2013/0028* (2013.01); *A61F 2013/00106* (2013.01)

(58) Field of Classification Search
  CPC ........ A45F 5/022; A45F 2200/05; A45F 5/00; A61F 13/00072; A61F 2013/0028; A61F 2013/00106; A61F 17/00; A45C 11/00; A45C 2011/007
  USPC .................................. 224/230, 218, 219, 222
  See application file for complete search history.

(56) References Cited

U.S. PATENT DOCUMENTS

| | | | | |
|---|---|---|---|---|
| 3,124,806 | A * | 3/1964 | Campbell | A63B 71/146 |
| | | | | 2/160 |
| 3,189,073 | A * | 6/1965 | Todd | A45C 1/04 |
| | | | | 224/222 |
| 3,438,062 | A * | 4/1969 | Curzon | A41D 27/20 |
| | | | | 2/247 |
| 4,429,793 | A * | 2/1984 | Ehmann | A61M 5/003 |
| | | | | 206/570 |
| 4,905,857 | A * | 3/1990 | Her | A45C 11/22 |
| | | | | 190/28 |
| 5,003,637 | A * | 4/1991 | Lonon | A41D 19/0024 |
| | | | | 2/160 |
| 5,009,222 | A * | 4/1991 | Her | A45C 11/22 |
| | | | | 206/811 |
| 5,379,491 | A | 1/1995 | Solo | |
| 5,423,419 | A * | 6/1995 | Wentz | A45C 11/04 |
| | | | | 206/6 |
| D386,611 | S * | 11/1997 | Sheu | D3/215 |
| 5,865,314 | A * | 2/1999 | Jacober | A61J 1/165 |
| | | | | 150/117 |
| 6,431,420 | B1 * | 8/2002 | Cragg | A45F 5/00 |
| | | | | 224/222 |
| 6,935,133 | B2 * | 8/2005 | Keeter | A61M 5/003 |
| | | | | 62/371 |
| 8,960,430 | B2 * | 2/2015 | Roach | A45C 13/02 |
| | | | | 206/363 |
| 9,938,042 | B1 * | 4/2018 | Aryanpanah | B65D 50/04 |
| 9,943,150 | B2 * | 4/2018 | Morrow | A45C 7/0095 |
| 2004/0251285 | A1 * | 12/2004 | O'Neill | A45F 5/00 |
| | | | | 224/221 |
| 2005/0116003 | A1 * | 6/2005 | Butler | A45F 5/02 |
| | | | | 224/604 |
| 2005/0199715 | A1 | 9/2005 | Reid | |
| 2006/0124675 | A1 * | 6/2006 | Calicott | A45F 5/00 |
| | | | | 224/222 |
| 2006/0144883 | A1 * | 7/2006 | Kouloulias | A45C 1/04 |
| | | | | 224/222 |
| 2006/0151355 | A1 | 7/2006 | Oh | |
| 2006/0226180 | A1 | 10/2006 | Hubbell | |
| 2007/0164032 | A1 * | 7/2007 | Cronin | B65D 43/12 |
| | | | | 220/345.1 |
| 2008/0047990 | A1 * | 2/2008 | Morgan | A45F 5/00 |
| | | | | 224/222 |
| 2008/0141700 | A1 * | 6/2008 | Fuchs | F25D 3/08 |
| | | | | 62/371 |
| 2008/0312615 | A1 * | 12/2008 | Hunter | A41D 13/1245 |
| | | | | 604/345 |
| 2010/0083422 | A1 * | 4/2010 | Lebl | A41D 27/20 |
| | | | | 2/251 |
| 2010/0200627 | A1 | 8/2010 | Marc | |
| 2012/0185999 | A1 * | 7/2012 | Raviv | A41D 27/205 |
| | | | | 2/247 |
| 2013/0043286 | A1 | 2/2013 | Kast | |
| 2013/0139298 | A1 | 6/2013 | Crump et al. | |
| 2015/0230528 | A1 * | 8/2015 | Knight | A41D 1/04 |
| | | | | 2/69 |

FOREIGN PATENT DOCUMENTS

| | | |
|---|---|---|
| CH | 429052 | 1/1967 |
| DE | 1891903 U | 4/1964 |
| DE | 9319888 | 5/1994 |
| DE | 20210863 U | 3/2003 |
| DE | 202009017918 U | 9/2010 |
| WO | 2009/029240 | 3/2009 |

OTHER PUBLICATIONS

International Search Report, PCT/NO2017/050073, dated Jun. 1, 2017.
Written Opinion, PCT/NO2017/050073, dated Jun. 1, 2017.
Norwegian Search Report, Norwegian Patent Application No. 20170362, dated Oct. 20, 2017.

\* cited by examiner

CARRYING BOX INTEGRATEABLE IN AN ARTICLE OF CLOTHING

CROSS-REFERENCE TO RELATED APPLICATIONS

This application is the U.S. national stage application of International Application PCT/NO2017/050073, filed Mar. 21, 2017, which international application was published on Sep. 28, 2017, as International Publication WO 2017/164748 in the English language. The International Application claims priority of Norwegian Patent Application No. 20160475, filed Mar. 21, 2016 and Norwegian Patent Application No. 20170362, filed Mar. 13, 2017. The international application and Norwegian applications are all incorporated herein by reference, in entirety.

FIELD

The invention concerns a carrying box releasably attachable to a portion of a piece of clothing, the carrying box comprising a top section connectable to a bottom section in a sealing manner, the bottom section comprising a curved bottom face with a curve radius substantially corresponding with the curve shape of a body part of a human being to be covered by said portion of piece of clothing, the carrying box further being arranged for releasable interconnection with said portion of piece of clothing by means of at least one attachment means.

BACKGROUND

People exposed to risk of injuries during their activities, especially people working in remote areas, i.e. lumberjacks, construction workers, farmers, etc., are in need of rapid access to first-aid means. A first-aid box present on site, i.e. in a construction machine, in a tractor, in a workmen's hut, etc. is useful for those working in or close to such a site. For people staying remote from such site, it is an advantage to carry first aid means. However, first aid means carried in a pocket or the like might is easily drop out, being damaged or lost, or left behind in the cloths and being destroyed when delivered to the laundry.

There is also a need for safe and easy access storage of other small means to be carried during an activity.

US2005116003A1 discloses a sealed box with a hinged cover and arranged to be carried by a user in a length adjustable strap or a clip. The box has a rectangular cross section with rounded edges.

US2004251285A1 discloses a wrist-mounted circular or polygonal storage box provided with straps. The box is provided with a curved bottom face and a hinged cover. One or more apertures are formed in the box to provide for phone antenna and earphone cables.

DE1891903U discloses a box arranged for carrying tickets etc., the box being provided with a curved length section and strap or clip shaped attachment means arranged for attaching the box to an arm, waist or the like. A hinged or displaceable cover is extending over approximately half the convex face of the box.

DE20210863U1 describes a small bag or holder arranged to be attached to an arm or a leg of a carrier by means of an elastic material.

U.S. Pat. No. 5,003,637 A describes a container that is removably attached to the external back of a glove by means of a hook-and-loop fastener (VELCRO) strip.

SUMMARY

The invention has for its object to remedy or to reduce at least one of the drawbacks of the prior art, or at least provide a useful alternative to prior art.

The object is achieved through features, which are specified in the description below and in the claims that follow.

A carrying box is provided, the box being arranged to accommodate bandage means, tools like scissor, tweezers, etc. useful when bandaging, small quantities of drugs like pain-killer tablets, and other means to be safely carried integrated in an article of clothing without being damaged during the carrier's activities. A bottom section with a curved bottom face is provided with sidewalls arranged for abutment against a periphery portion of a top section. At least one of the bottom section and the top section is provided with sealing means arranged for fluid tight sealing of the carrying box at least when connecting means are engaging the bottom section and the top section in a locking manner. The sealing provides a carrying box that can remain integrated in the piece of clothing during the cleaning of said piece of clothing in a washing machine without damaging the content of the carrying box. Thus, the risk of the carrier to leave a redressing site without the carrying box is avoided.

The carrying box is arranged to carry a compress element, i.e. an element that is used to apply sufficient pressure upon a wound to stop bleeding, the compress and the carrying box held in position by means of a surrounding bandage. The curved bottom face may temporarily carry the compress element by solely providing support to the compress element, or the compress element may be temporarily attached to the bottom face by means of adhesive tape hook-and-loop fasteners (VELCRO strips) or the like. Likewise, the carrying box as a whole or the bottom section alone can be used as a compress by positioning the curved face of the bottom section on a site in need of compress to stop bleeding. A compress element may be integrated in the top section, extending from an inward top face. The integrated compress element is preferably made of a resilient material. The compress element may be releasable, possibly arranged to be used even when separated from the top section.

The carrying box is arranged for releasably attachment to the exterior of a portion of an article of clothing. The portion of the article of clothing might be a sleeve of a jacket, a shirt or coveralls, or a leg of a trouser or coveralls. The carrying box and the portion of the article of clothing are provided with corresponding attachment means arranged for easy attachment of the carrying box to the clothing to ease the preparation of the carrying box for operating state, and, most important, easy removal of the carrying box from the clothing in a situation of need of fast access to the content of the carrying box. The attachment means might be VELCRO strips (hook and loop fasteners), push buttons, zip-fasteners, a pocket, etc.

The curved bottom face of the carrying box is preferably adapted to the curved cross sectional form of a thigh or an upper arm of a human being. The axial direction of the curved bottom face is preferably coinciding with the longitudinal direction of the carrying box. The radius of the curved bottom face is preferably in the range of 200-300 mm, more preferably in the range of 220-280 mm, and even more preferably in the range of 240-260 mm.

Transitions between bottom face and the sidewalls of the bottom section might be rounded, preferably with a radius in the range of 4-8 mm.

An advantage of the curved shape of the bottom face and the rounded sidewall transitions is that the carrying box is gentle to an adjacent body part carrying said piece of clothing.

The minimum clearance between the internal bottom face and internal top face is preferably in the range of 18-27 mm, more preferably in the range of 19-25 mm, and even more preferably in the range of 20-23 mm.

The connecting means are preferably two opposing snap fasteners. The advantage of this way of connecting the top section and the bottom section is that the carrying box is openable whichever of the two snap fasteners is released.

Alternatively, the connecting means may be a hinge and at least one snap fastener. The at least one snap fastener is preferably opposing the hinge.

The top face is preferably curved. A curve axis of the top face is preferably coinciding with a curve axis of the bottom face when the carrying box is in a closed state.

The invention is defined by the independent patent claims. The dependent claims define advantageous embodiments of the invention.

The carrying box is made of a heat resistant and flame retardant material, possibly satisfying the requirements of ISO 1043-4.

In a first aspect, the invention more specifically relates to a carrying box releasably attachable to a portion of a piece of clothing, the carrying box comprising a top section connectable to a bottom section in a sealing manner, the bottom section comprising a curved bottom face with a curve radius substantially corresponding with the curve shape of a body part of a human being to be covered by said portion of piece of clothing, the carrying box further being arranged for releasable interconnection with said portion of piece of clothing by means of at least one attachment means, characterised in that at least one of an inward top face of the top section and the bottom face of the bottom section is arranged to carry a compress element.

The compress element may be integrated inside the top section, extending from the inward top face.

The compress element may be releasably attached to the inward top face of the top section.

The compress element may be temporarily attached to the curved bottom face.

The compress element may be made of a resilient material.

The attachment means may be a pocket integrated in the piece of clothing. Alternatively, the attachment means may be collected from the group comprising hook and loop fastener (VELCRO), push button and zip-fastener.

The curve radius of the curved bottom face may be in the range of 200-300 mm, more preferably in the range of 220-280 mm, and even more preferably in the range of 240-260 mm.

A curve axis of a top face of the top section may coincide with a curve axis of the bottom face when the carrying box is in a closed state.

The top section may be connected to the bottom section by means of at least one connecting means arranged to engage with corresponding locking element attaching portions integrated in sidewalls of the top section and the bottom section. Alternatively, the top section may be connected to the bottom section by means of a hinge and at least one snap fastener opposing said hinge and arranged to engage with corresponding link element attaching portions integrated in sidewalls of the top section and the bottom section.

The minimum internal clearance between the bottom face and the top face may be in the range of 18-27 mm, more preferably in the range of 19-25 mm, and even more preferably in the range of 20-23 mm.

In a second aspect, the invention more specifically relates to a piece of clothing comprising a carrying box according to the first aspect of the invention, releasably attached to a portion of the piece of clothing.

BRIEF DESCRIPTION OF THE DRAWINGS

In the following is described examples of preferred embodiments illustrated in the accompanying drawings, wherein.

DETAILED DESCRIPTION OF THE DRAWINGS

A carrying box 1 comprises a bottom section 11 and a mating top section 12, the bottom section 11 and top section 12 being interconnectable in a sealing way by means of several connecting means 13 to define a closed volume arranged for accommodating bandage, small tools, small quantities of medicines, etc. (not shown).

Figure 1:
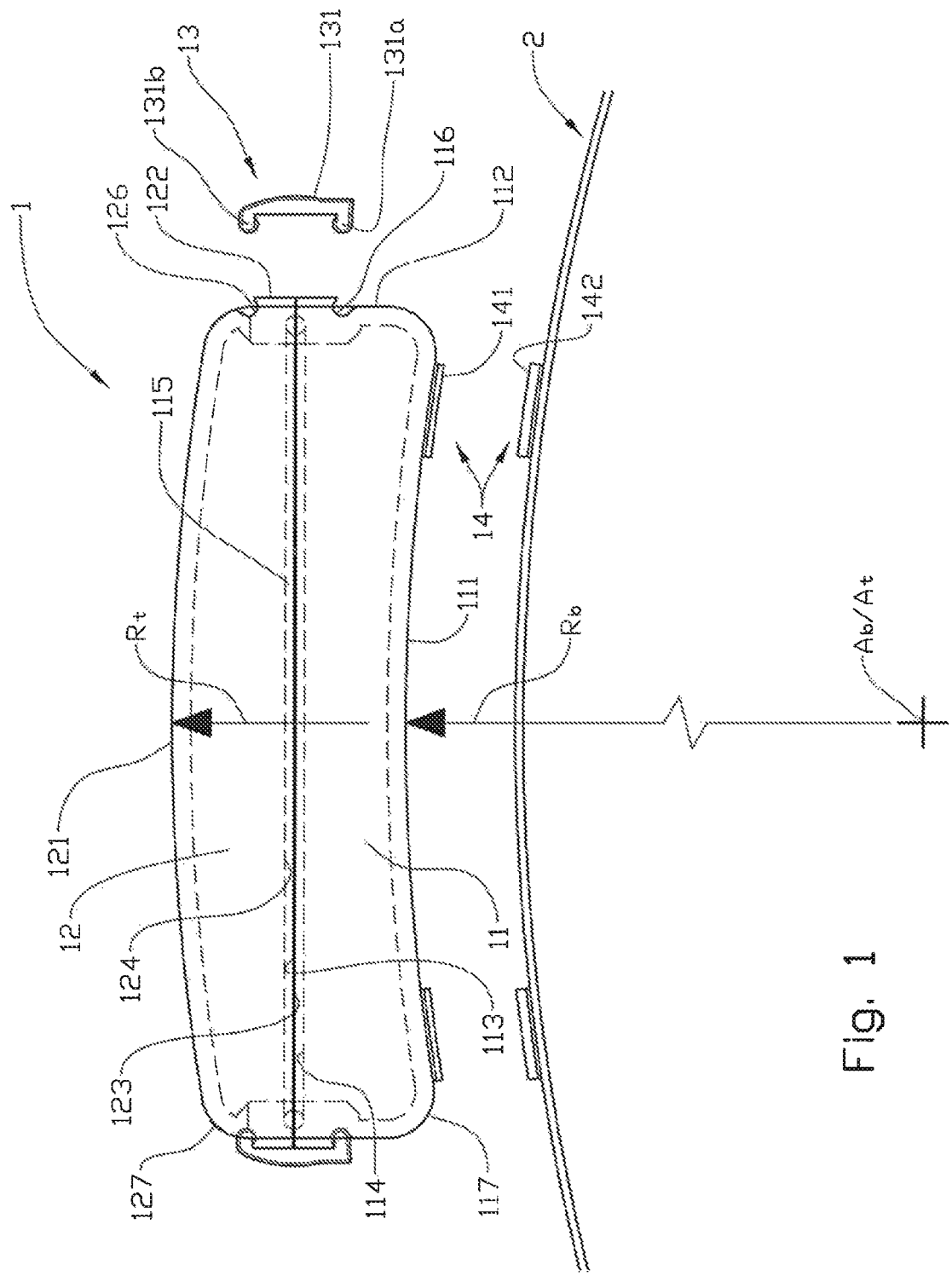
FIG. 1 is an end view of a first embodiment of a carrying box according to the invention in a closed state.
Figure 2:
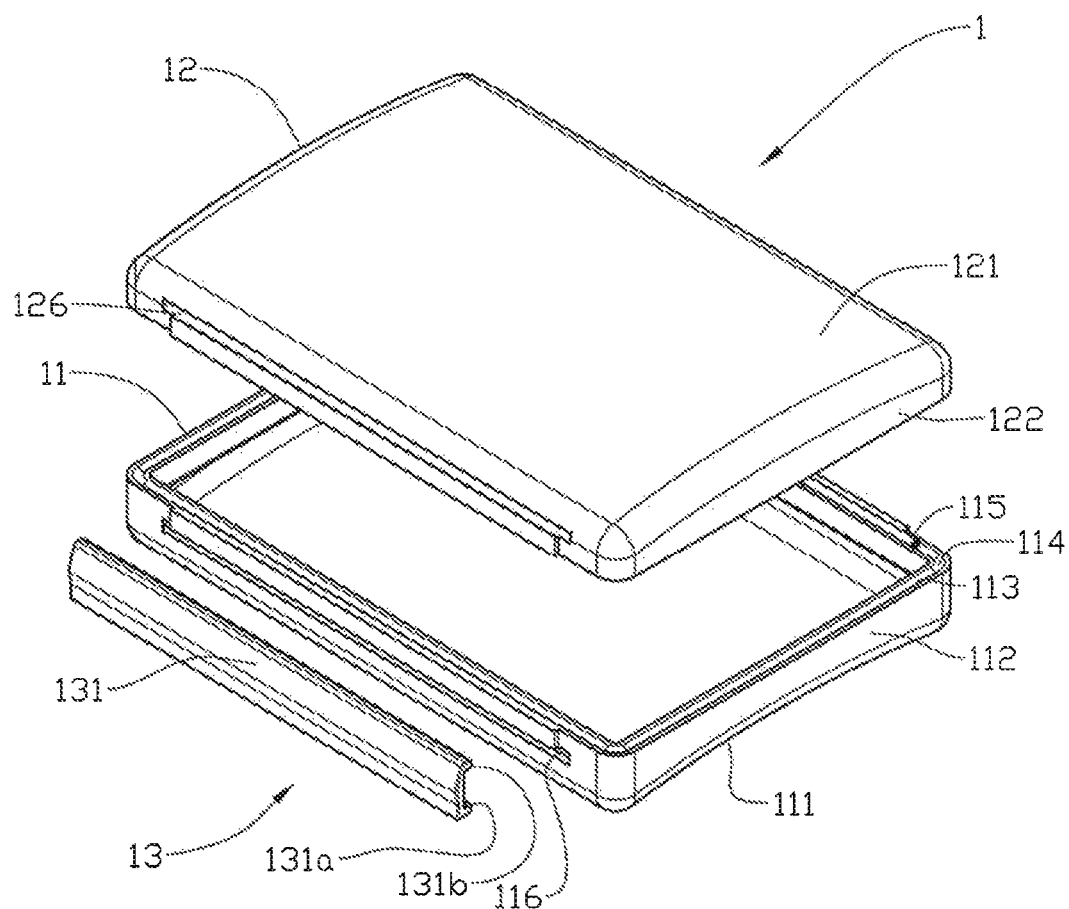
FIG. 2 is an exploded perspective view of the carrying box showing one locking means in front of the carrying box only.

The bottom section 11 comprises a curved bottom face 111 with a curve radius $R_b$ and a curve axis $A_b$ (see FIG. 1). The bottom face 111 is defined by bottom sidewalls 112 forming a bottom abutment portion 113, in the shown embodiments formed straight. The bottom face 111 and the sidewalls 112 are forming a continuous, rounded transition portion 117 with a radius in the range of 4-8 mm. The bottom abutment portion 113 includes a continuous bottom seal seat 114 arranged to hold a seal 115, in FIG. 2 shown in part only.

The top section 12 comprises a curved top face 121 with a curve radius $R_t$ and a curve axis $A_t$ coinciding with the bottom curve axis $A_b$ when the top section 12 is mating the bottom section 11. The top face 121 is defined by top sidewalls 122 forming a top abutment portion 123 arranged with a top seal seat 124 to abut against the seal 115 in a sealing manner when the carriage box 1 is in a closed state. The top face 121 and the sidewalls 122 are forming a continuous, rounded transition portion 127 with a radius in the range of 4-8 mm.

In a preferred embodiment, shown in FIG. 1, the bottom section 11 and the top section 12 are interconnected by means of two locking elements 131 comprising a first snap portion 131a and a second snap portion 131b arranged for releasable engagement with corresponding locking element engagement portions 116, 126 provided in corresponding sidewalls 112, 122 of the bottom section 11 and top section 12.

Figure 3:
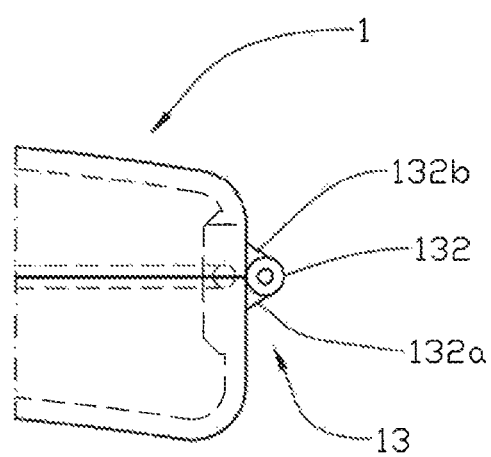
FIG. 3 is a partial side view of a hinged embodiment of the carrying box.

In an alternative embodiment, see FIG. 3, one locking element 131 is replaced by a hinge 132, said hinge 132 interconnecting the bottom section 11 and top section 12 by means of a bottom hinge portion 132a meshing a top hinge portion 132b.

Figure 4:
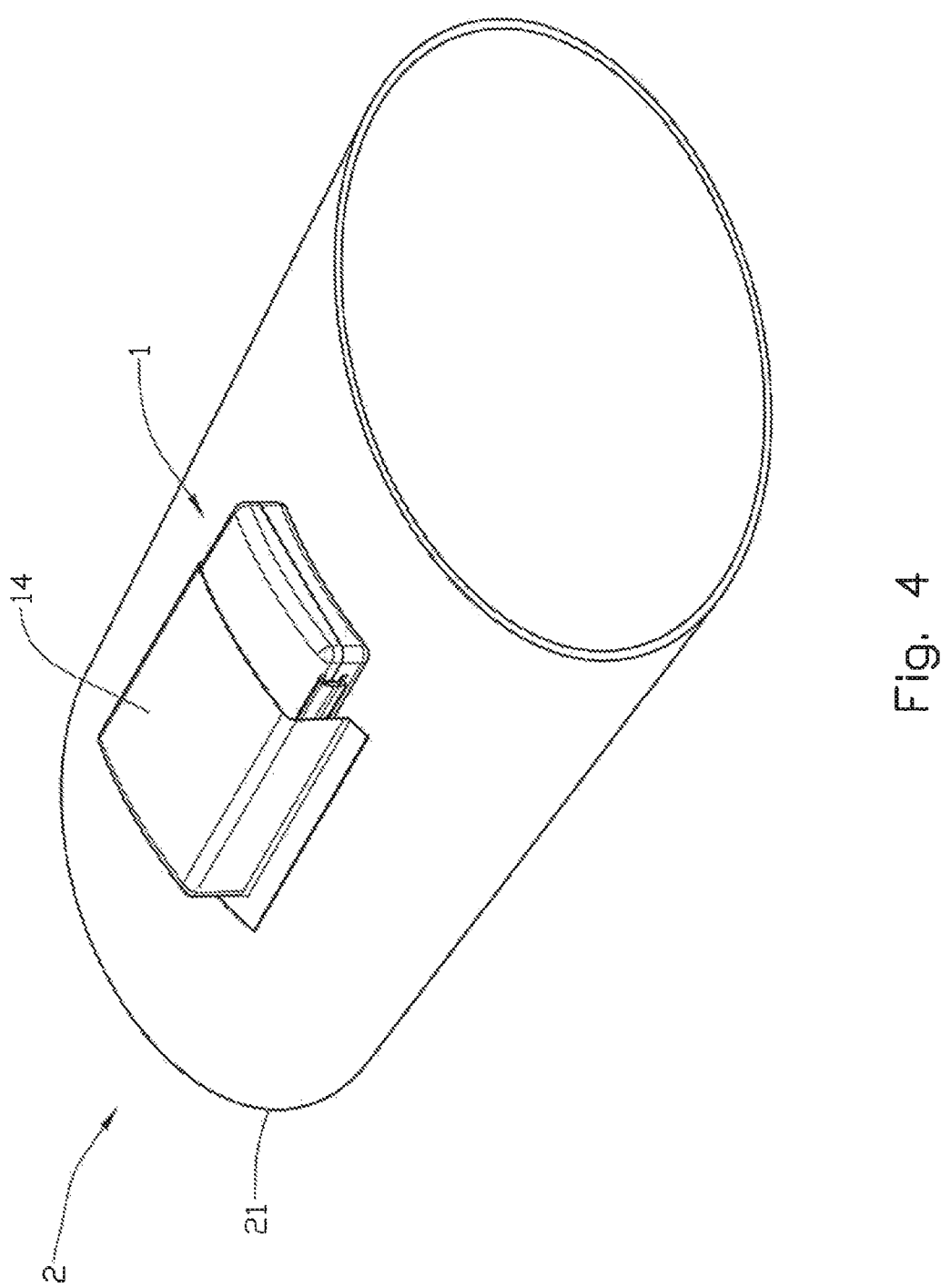
FIG. 4 is a perspective view of the carrying box accommodated in a pocket on a piece of clothing.
Figure 5:
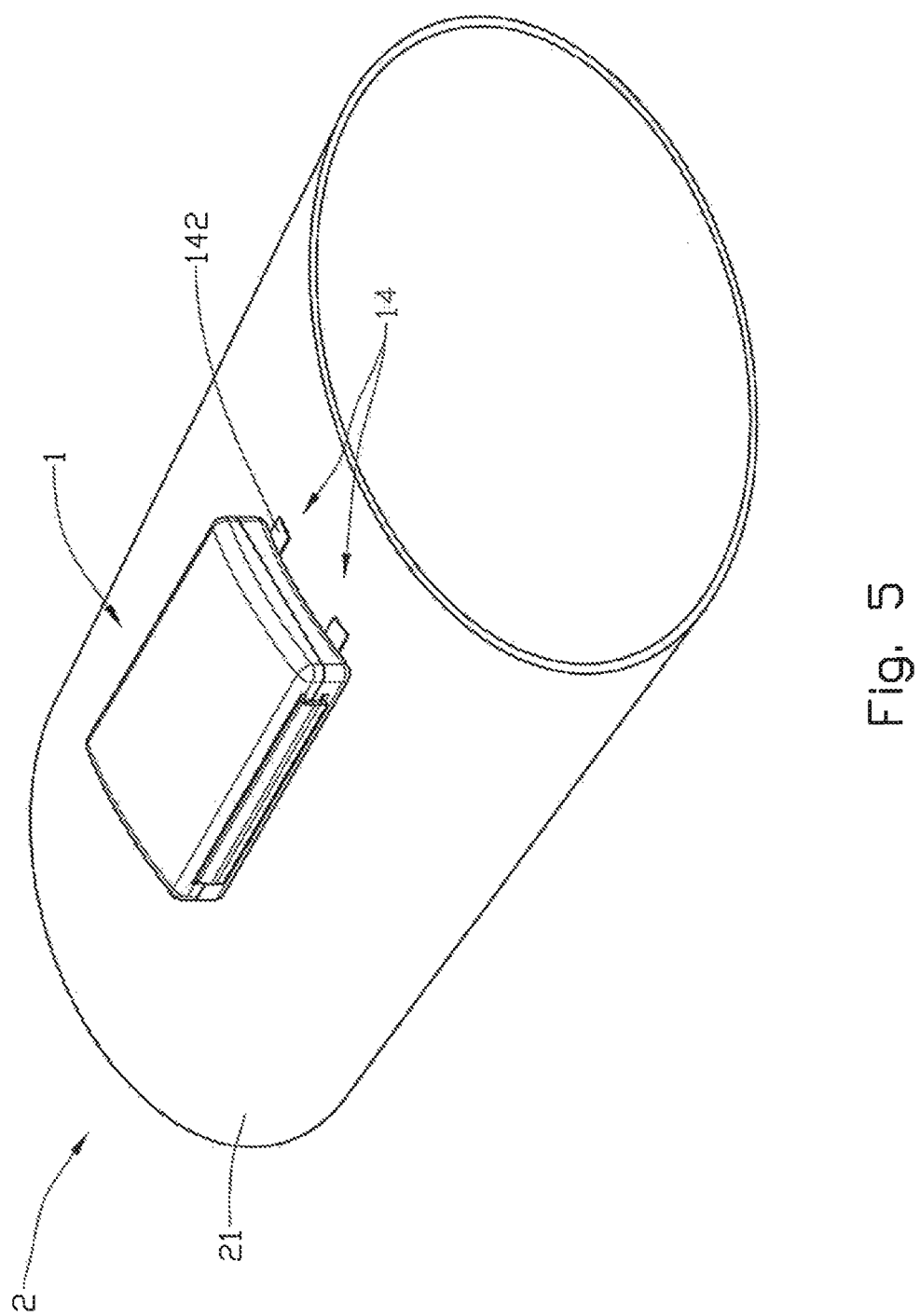
FIG. 5 is a perspective view of the carrying box attached to a piece of clothing by means of hook-and-loop fasteners (VELCRO strips)

The curve shape of the bottom face 111 is substantially corresponding with the curved shape of is body part being covered by a portion 21 of a piece of clothing 2, to which the carrying box 1 can be attached by means of at least one attachment means 14, see FIGS. 4 and 5. In a preferred embodiment, the carrying box 1 is hold by an attachment means in the form of a pocket 14, see FIG. 4. In an alternative embodiment (see FIGS. 1 and 5), the carrying box 1 may be attached to the piece of clothing 2 by means first attachment means 141 arranged on the carrying box 1 and mating corresponding second attachment means 142 integrated in a convenient portion of the piece of clothing 2, here schematically shown as hook and loop fasteners (VELCRO) strips. The mating attachment means 141, 142 may alternatively be provided as push buttons, zip-fasteners, etc.

The curved shape of the bottom face 111 is suitable for supporting a compress element (not shown), possibly temporary attached to the bottom face by means of a third attachment means 143 (see FIG. 6), e.g. adhesive tape or VELCRO strips. Furthermore, the curved bottom face can provide compress without the use of a separate compress element applied thereto.

Figure 6:
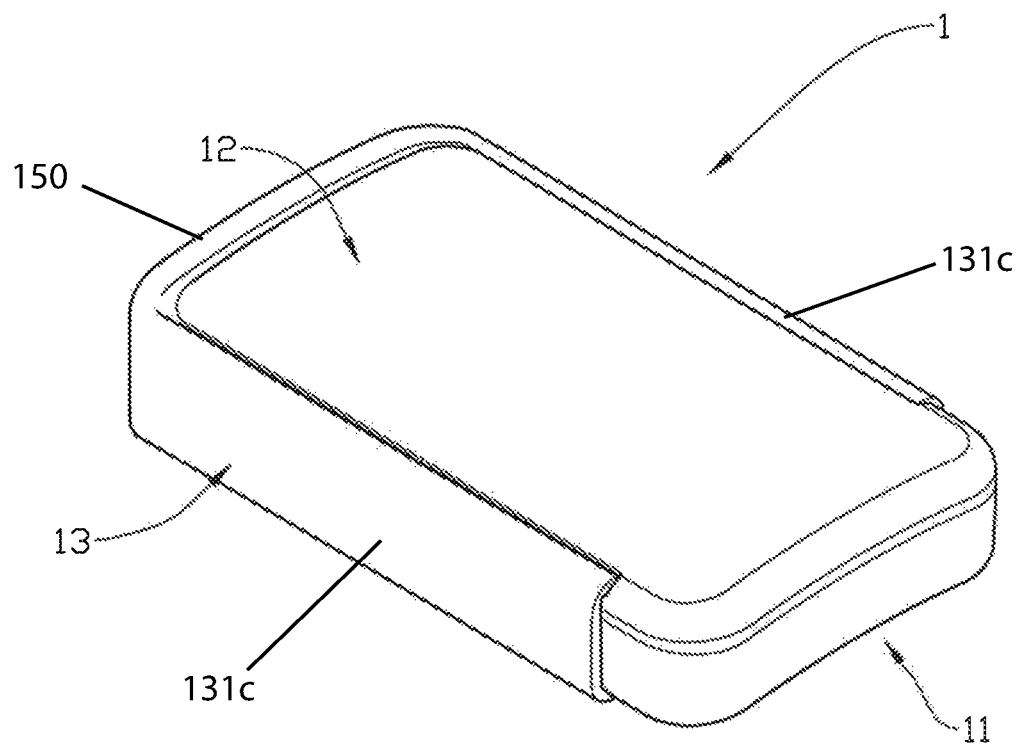
FIG. 6 is a perspective view of a second embodiment of the carrying box in a closed state and provided with a slidable, bow shaped connecting means.
Figure 7:
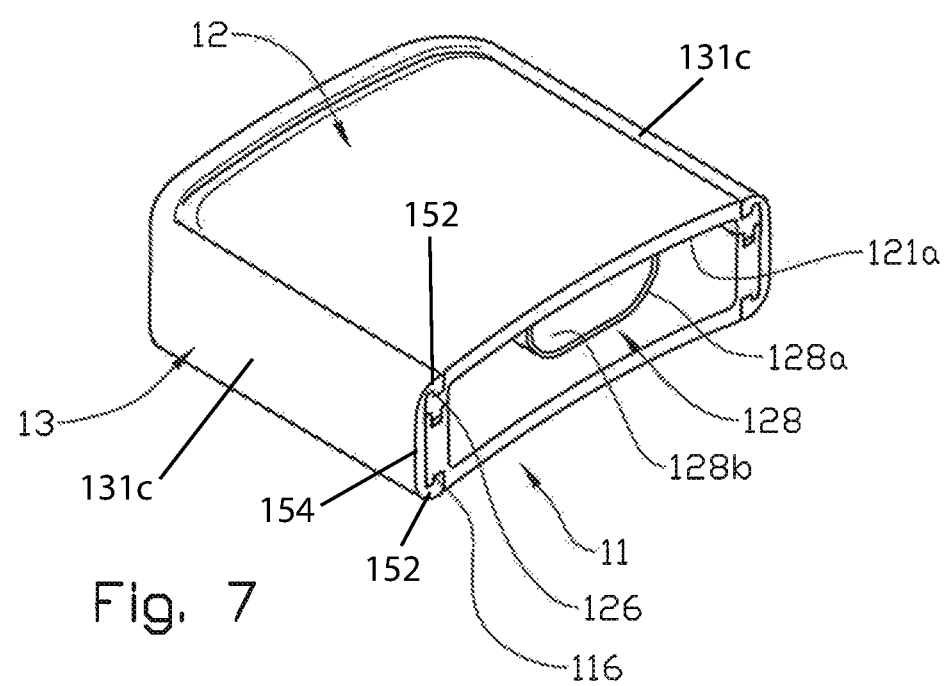
FIG. 7 is a perspective cross sectional view of the second embodiment of the carrying box with a plate shaped compress element arranged inside a top cover.
Figure 8:
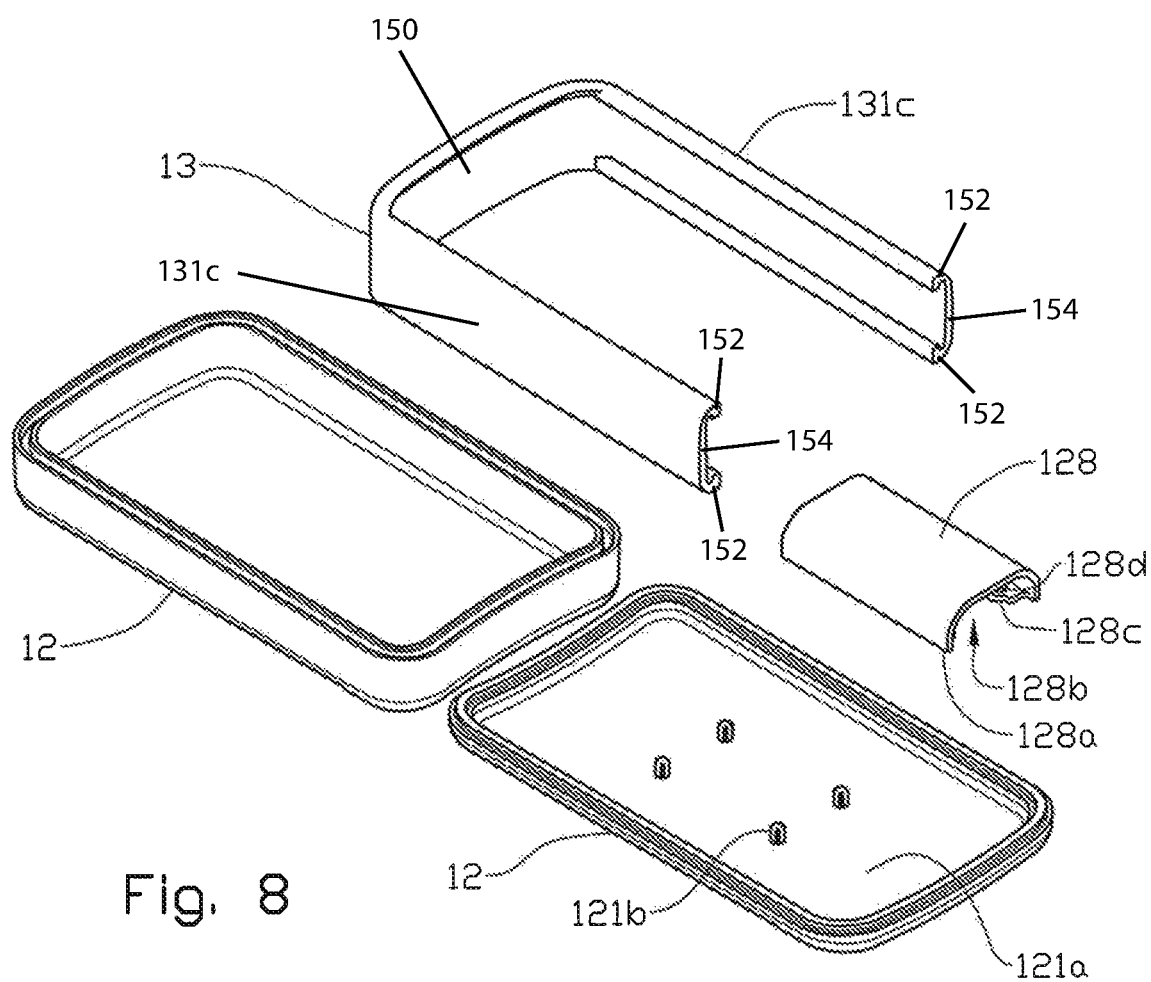
FIG. 8 is an exploded perspective view of the second embodiment of the carrying box, the top cover turned upside down.

It is now referred to FIGS. 6, 7 and 8, wherein still another alternative embodiment is shown. Inside the top section 12, on an inward top face 121a a compress element 128 is attached (see FIGS. 7 and 8). The compress element 128 might be made of a resilient block material, e.g. cell foam (not shown), or a plate element 128a. The plate element 128a shown in FIGS. 7 and 8 defines a void 128b with open ends that may be used for storage purposes even when in an operative state compressing a wound. The plate element 128a is preferably made of a resilient material. The void 128b inside the plate element 128a might hold one or more items in its idle and active state, for example bandage materials.

The compress element 128 may be releasably attached to the inward to face 121a by means of suitable attachment means, in FIG. 9 shown as lugs 128c with cut-outs 128d provided in the void 128b and arranged to receive corresponding pins 121b protruding from the inward top face 121a.

In this embodiment, the connecting means 13 is formed as a bow shaped element wherein parallel slider portions 131c are arranged for slidable engagement with the corresponding engagement portions 116, 126 of the abutting bottom and top sections 11, 12, respectively. As illustrated in FIGS. 6-8, some embodiments of the connecting means 13 can be generally U-shaped and include a connecting wall 150 that extends between the two parallel slider portions 131c. The slider portions 131c, which are positioned proximate opposite ends of the connecting wall 150, each project outward from the connecting wall 150 in the same direction so that the slider portions 131c are parallel to each other. One of the slider portions 131c can be configured to engage engagement portions 116, 126 extending from a first side of the top and bottom sections 11, 12 (for example, a left side), and the second one of the slider portions can be configured to engage engagement portions 116, 126 extending from a second side of the top and bottom sections 11, 12 (for example, a right side), which may be opposite the first side. Each of the parallel slider portions 131c can include two channels 152 positioned on opposite ends of a vertical wall 154. The channels 152 are oriented such that they each face inward and open towards the opposite channel 152 at the other end of the vertical wall 154. To secure the top section 12 to the bottom section, the channel 152 positioned at the top side of the vertical wall 154 on each of the slider portions 131c is configured to slidably engage the engagement portion 126 projecting from a corresponding side of the top section 12, and the channel 152 positioned at the bottom side of the vertical wall 154 on each of the slider portions 131c is configured to slidably engage the engagement portion 116 projecting from a corresponding side of the bottom section 11.

The requirements of the attachment means are to provide secure attachment of the carrying box 1 during the regular actions performed by the carrier during his/her work, and still offer the possibility of easy and quick detachment of the carrying box 1 when there is a need of rapid access to the content of the carrying box, for example in an emergency situation where the worker is in need of bandages.

The sealing of the carrying box 1 allows the carrying box 1 to be exposed to water without damaging the content of the carrying box 1. The exposure to water includes contact with rain and snow, and unintentional stay in water, for example in a washing machine.

The entire carrying box 1 is preferably made of materials that can withstand detergents, hot water is and UV radiations. Furthermore, lightweight materials are preferred. Various types of plastic suitable for injection moulding are preferred.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements.

The mere fact that certain measures are recited in mutually different dependent claims does not indicate that a combination of these measures cannot be used to advantage.

The invention claimed is:

1. A carrying box releasably attachable to a portion of a piece of clothing, the carrying box comprising
   a top section connectable to a bottom section in a fluid sealing manner,
   the bottom section comprises a curved bottom face with a curve radius corresponding with the curve shape of a body part of a human being to be covered by said portion of piece of clothing,
   the carrying box further being arranged for releasable interconnection with said portion of piece of clothing via at least one attachment means, wherein the carrying box further comprises:
   a compress element configured to be removably secured to an inward top face of the top section; and
   a bow shaped connecting means for connecting the top section to the bottom section, the bow shaped connecting means having parallel slider portions arranged for slidable engagement with corresponding locking element attaching portions integrated in sidewalls of the bottom section and the top section;

wherein each of the parallel slider portions includes a vertical wall and two channels positioned on opposite ends of the vertical wall, each of the channels facing inward towards the other one of the channels; and wherein the channels are configured to slidably receive a corresponding one of the locking element attaching portions of the bottom section and the top section.

2. The carrying box according to claim 1, wherein the compress element is integrated inside the top section, extending from the inward top face.

3. The carrying box according to claim 1, wherein the compress element is releasably attached to the inward top face of the top section.

4. The carrying box according to claim 1, wherein the compress element is made of a resilient material.

5. The carrying box according to claim 1, wherein the attachment means is a pocket integrated in the piece of clothing.

6. The carrying box according to claim 1, wherein the curve radius of the curved bottom face is in the range of 200-300 mm.

7. The carrying box according to claim 1, wherein the curve radius of the curved bottom face is in the range of 220-280 mm.

8. The carrying box according to claim 1, wherein the curve radius of the curved bottom face is in the range of 240-260 mm.

9. The carrying box according to claim 1, wherein a curve axis of a top face of the top section is coinciding with a curve axis of the bottom face when the carrying box is in a closed state.

10. The carrying box according to claim 1, wherein the minimum internal clearance between the bottom face and the top face is in the range of 18-27 mm.

11. The carrying box according to claim 1, wherein the minimum internal clearance between the bottom face and the top face is in the range of 19-25 mm.

12. The carrying box according to claim 1, wherein the minimum internal clearance between the bottom face and the top face is in the range of 20-23 mm.

13. The carrying box of claim 1, wherein a first one of the parallel slider portions if configured to slidably engage locking element attaching portions on a first side of the bottom section and the top section, and a second one of the parallel slider portions if configured to slidably engage locking element attaching portions on a second side of the bottom section and the top section opposite the first side.

14. A carrying box releasably attachable to a portion of a piece of clothing, the carrying box comprising a top section connectable to a bottom section in a fluid sealing manner, the bottom section comprises a curved bottom face with a curve radius corresponding with the curve shape of a body part of a human being to be covered by said portion of piece of clothing, the carrying box further being arranged for releasable interconnection with said portion of piece of clothing via at least one attachment means, wherein the carrying box further comprises:

a compress element configured to be removably secured to an inward top face of the top section; and a bow shaped connecting means for connecting the top section to the bottom section, the bow shaped connecting means having parallel slider portions arranged for slidable engagement with corresponding locking element attaching portions integrated in sidewalls of the bottom section and the top section;

wherein the bow shaped connecting means is U-shaped and includes a connecting wall extending between the parallel slider portions, which project outward from opposite ends of the base wall.

15. A carrying box releasably attachable to a portion of a piece of clothing, the carrying box comprising a top section connectable to a bottom section in a fluid sealing manner, the bottom section comprises a curved bottom face with a curve radius corresponding with the curve shape of a body part of a human being to be covered by said portion of piece of clothing, the carrying box further being arranged for releasable interconnection with said portion of piece of clothing via at least one attachment means, wherein the carrying box further comprises:

a compress element configured to be removably secured to an inward top face of the top section; and a bow shaped connecting means for connecting the top section to the bottom section, the bow shaped connecting means having parallel slider portions arranged for slidable engagement with corresponding locking element attaching portions integrated in sidewalls of the bottom section and the top section;

wherein the compress element includes at least one cutout configured to receive a pin protruding from the inward top face of the top section; and wherein engagement between the at least one cutout and the pin is configured to secure the compress element to the inward top face of the top section.

\* \* \* \* \*